(12) United States Patent
Bond et al.

(10) Patent No.: US 9,730,889 B2
(45) Date of Patent: Aug. 15, 2017

(54) STEROID-SPARING EFFECTS OF BETA-ADRENERGIC INVERSE AGONISTS AND USES THEREOF

(75) Inventors: Richard A. Bond, Houston, TX (US);
Burton F. Dickey, Houston, TX (US);
Michael J. Tuvim, Houston, TX (US)

(73) Assignee: University of Houston System, Houston, TX (US)

( * ) Notice: Subject to any disclaimer, the term of this patent is extended or adjusted under 35 U.S.C. 154(b) by 191 days.

(21) Appl. No.: 13/466,498

(22) Filed: May 8, 2012

(65) Prior Publication Data

US 2012/0289488 A1    Nov. 15, 2012

Related U.S. Application Data

(60) Provisional application No. 61/518,622, filed on May 9, 2011.

(51) Int. Cl.
| | | |
|---|---|---|
| *A61K 31/573* | (2006.01) | |
| *A61K 31/137* | (2006.01) | |
| *A61K 9/00* | (2006.01) | |
| *A61K 45/06* | (2006.01) | |
| *A61K 47/26* | (2006.01) | |

(52) U.S. Cl.
CPC .......... *A61K 9/0075* (2013.01); *A61K 31/573* (2013.01); *A61K 45/06* (2013.01); *A61K 47/26* (2013.01)

(58) Field of Classification Search
CPC ..... A61K 31/60; A61K 31/165; A61K 31/573
USPC ....................................................... 514/171
See application file for complete search history.

(56) References Cited

U.S. PATENT DOCUMENTS

| | | | | |
|---|---|---|---|---|
| 4,904,649 A | * | 2/1990 | Schwartz | 514/171 |
| 5,212,168 A | * | 5/1993 | Schwartz | 514/179 |
| 5,674,860 A | * | 10/1997 | Carling et al. | 514/171 |
| 7,528,175 B2 | * | 5/2009 | Bond | 514/649 |

* cited by examiner

*Primary Examiner* — Jennifer M Kim
(74) *Attorney, Agent, or Firm* — Benjamin Aaron Adler (57) ABSTRACT

Provided herein is a pharmaceutical composition combination which comprises (a) a corticosteroid and (b) b-adrenergic receptor antagonist characterised in that active ingredients (a) and (b) form part of a single composition. Further provided is a method of treating a human or animal patient suffering from or susceptible to a respiratory disease or condition, said method comprises simultaneously, concurrently, separately or sequentially administering to the patient an effective amount of a b-adrenergic receptor antagonist and a corticosteroid.

13 Claims, 5 Drawing Sheets

No OVA

FIG. 3A

OVA, NAD 25

FIG. 3D

OVA, No Rx

FIG. 3B

OVA, Dex + NAD

FIG. 3E

OVA, Dex 0.4

STEROID-SPARING EFFECTS OF BETA-ADRENERGIC INVERSE AGONISTS AND USES THEREOF

CROSS-REFERENCES TO RELATED APPLICATIONS

This non-provisional application claims benefit of provisional application U.S. Ser. No. 61/518,622, filed May 9, 2011, now abandoned, the entirety of which is hereby incorporated by reference.

FEDERAL FUNDING LEGEND

This invention was made with governmental support under Grant Number 5R01A1079236-02 awarded by the National Institutes of Health. The government has certain rights in this invention.

BACKGROUND OF THE INVENTION

Field of the Invention

The present invention relates generally to field of pharmacotherapy of asthma. More specifically, the present invention discloses a method of co-administering beta-adrenergic antagonists with inverse agonist activity and corticosteroids allowing for a significant reduction of steroid levels without any loss in the anti-inflammatory ability.

Description of the Related Art

Asthma is a common chronic inflammatory disease of the airways characterized airway hyper responsiveness, by reversible airflow obstruction and poorly reversible airway remodeling (1). A distinguishing feature of asthma is airway infiltration by inflammatory cells such as $T_H2$ lymphocytes and eosinophils (2), generating a broad range of inflammatory mediators. One consequence of this inflammation is changes to the surface epithelium of intrapulmonary airways, which acquire a mucus producing, goblet cell phenotype (1, 3-5). Glucocorticosteroids are the most effective treatment available for the long term management of asthma (6-7). These drugs reduce asthma symptoms (6-7), reduce the risk of asthma exacerbations (8), and improve the quality of life (9-10). In addition, glucocorticosteroids reduce inflammation (7, 11-12) and mucous metaplasia (13-14).

Despite their proven efficacy in persistent asthma, enthusiasm for glucocorticosteroid use is tempered by concern about their adverse effects. These adverse effects, such as cataracts have been shown to be positively correlated with the dose of inhaled glucocorticosteroids (15-17). Indeed, in some patients long-term use of high doses of inhaled glucocorticosteroids can produce a similar side effect profile to that of oral steroid use, including reduction in growth velocity, cataracts, glaucoma, osteoporosis, and fractures (18).

Therefore, the availability of additional effective anti-inflammatory agents that could lower the required dose of glucocorticosteroids would be advantageous. Such compounds have been termed 'steroid-sparing', implying that concomitant use will allow lower doses of steroid to be used without any loss of therapeutic efficacy. In an allergen-driven murine model of asthma, chronic administration of β-blockers, specifically $β_2$-adrenoceptor ($β_2$-AR) with inverse agonist activity, attenuated mucous metaplasia, airway hyperresponsiveness and inflammation (19-20). Furthermore, one of these β-blockers decreased airway hyperresponsiveness in mild asthmatics (21-22).

The prior art is deficient in steroid-sparing therapeutic regimens for the treatment of asthma. The present invention fulfills this longstanding need and desire in the art.

SUMMARY OF THE INVENTION

The present invention teaches that the simultaneous administration or co-administration) of low-dose beta-adrenergic antagonists with inverse agonist activity and corticosteroids is more effective at reducing both the level of eosinophils and the volume density of epithelial mucin than either drug given alone, while also showing fully additive therapeutic effects.

Thus, the present invention is directed to a pharmaceutical composition combination which comprises (a) a corticosteroid and (b) b-adrenergic receptor antagonist characterised in that active ingredients (a) and (b) form part of a single composition.

The present invention also is directed to a method of treating a human or animal patient suffering from or susceptible to a respiratory disease or condition, said method comprises simultaneously, concurrently, separately or sequentially administering to the patient an effective amount of a b-adrenergic receptor antagonist and a corticosteroid.

The present invention is directed further to a method of treating an inflammatory condition of the lung characterized by an increase in allergen-induced airway hyper-responsiveness and mucus-containing cells in a mammalian subject, said method comprising administering to said subject an effective amount of a b-adrenergic receptor antagonist and a corticosteroid thereof in an amount sufficient to decrease the lung inflammation in the subject, thereby treating the lung inflammatory condition in said subject.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 3A), OVA immunized mice administered vehicle (FIG. 3B; No Rx), dexamethasone (FIG. 3C; OVA, Dex), (black), nadolol (FIG. 3D; OVA, NAD 25), (white), or a combination dose of dexamethasone and nadolol (FIG. 3E; OVA, Dex+ NAD), (stripes). Scale bar, 20 µm. Morphometric quantification of the mucin volume density was assessed from the various groups; No OVA—stripes, No Rx—stripes, Dex— white, Nad—black, and Dex+Nad–gray (FIG. 3F). Values are the means±SEM of data from 4 to 5 mice in each group (n=4-5). *, indicate significant difference compared to No Rx, $P<0.05$; , indicate significant difference compared to 4.0 mg/kg/day dexamethasone treatment, $P<0.05$;  , indicate significant difference compared to 0.4 mg/kg/day dexamethasone treatment, $P<0.05$; ****, and indicate significant difference compared to 25 ppm nadolol treatment, $P<0.05$.

DESCRIPTION OF THE PREFERRED EMBODIMENTS

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device, compound, composition, or method described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "subject" refers to any recipient of a composition or pharmaceutical composition comprising a beta-adrenergic receptor antagonist, preferably with inverse agonist activity, with or without a corticosteroid as described herein. Preferably, the subject is a mammal, for example, a human or animal subject.

The present invention relates to methods of administering beta-adrenergic antagonists, particularly with inverse agonist activity, or beta-blockers in combination with other medications to enhance the treatment of asthma. More specifically, the present invention discloses a method of co-administering nadolol and corticosteroids, such as but not limited to dexamethasone, to allow for a significant reduction of steroid levels without any loss in the anti-inflammatory ability. The present invention finds important applications particularly for the use of beta-adrenergic antagonists with inverse agonist activity in steroid-sparing therapeutic regimen for the treatment of asthma.

Thus, the present invention is directed to a pharmaceutical composition combination which comprises (a) a corticosteroid and (b) b-adrenergic receptor antagonist characterised in that active ingredients (a) and (b) form part of a single composition. Generally, in this composition, ingredients (a) and (b) are provided together with instructions for simultaneous, concurrent, separate or sequential administration, in a kit of parts for the treatment of a patient suffering from or susceptible to a respiratory disease. Representative examples of a respiratory disease which may be treated using this composition, include but are not limited to asthma, chronic obstructive pulmonary disease, cystic fibrosis or any diseases characterized by inflammation and/or excessive mucous in the airways.

Generally, any β-adrenergic receptor antagonist, such as with an inverse agonist activity, may be included in this composition. Representative examples of the β-adrenergic receptor antagonists used herein include, but are not limited to, nadolol, metoprolol, celiprolol, salbutamol, bisoprolol, betaxolol, atenolol, ICI-118,551 and carvedilol and optionally in the form of their racemates, their enantiomers, their diastereomers and mixtures thereof, and optionally their pharmacologically-compatible acid addition salts. Generally, any corticosteroid may be included in this composition. Representative examples of a corticosteroid include but are not limited to dexamethasone, budesonide, beclomethasone, triamcinolone, dexamethasone, mometasone, ciclesonide, fluticasone, flunisolide, dexamethasone sodium phosphate and esters thereof.

In one aspect of this composition, the active ingredients (a) and (b) are in the form a dry powder suitable for inhalation. In another aspect, the composition may further comprising a pharmaceutically acceptable excipient selected from mono-, di- or polysaccharides and sugar alcohols.

The present invention is further directed to a method of treating a human or animal patient suffering from or susceptible to a respiratory disease or condition, said method comprises simultaneously, concurrently, separately or sequentially administering to said patient an effective amount of a b-adrenergic receptor antagonist and a corticosteroid. Representative examples of a respiratory disease which may be treated using this composition are as described supra.

Generally, any beta-adrenergic receptor antagonist with inverse agonist activity may be included in this method. Representative examples of a b-adrenergic receptor antagonist are as described supra. Generally, any corticosteroid may be included in this method. Representative examples of a corticosteroid also are as described supra. Preferably, in this method, the b-adrenergic receptor antagonist is administered in an amount of from about 1% to about 100% of the FDA approved doses of each agent to about and the corticosteroid is administered in an amount of from about 0.1% to about 100% of the FDA approved doses of each agent.

The present invention is further directed to a method of treating an inflammatory condition of the lung characterized by an increase in allergen-induced airway hyper-responsiveness and mucus-containing cells in a mammalian subject, where the method comprises administering to the subject an effective amount of a b-adrenergic receptor antagonist and a corticosteroid thereof in an amount sufficient to decrease the lung inflammation in the subject, thereby treating the lung inflammatory condition in said subject. Representative examples of a respiratory disease which may be treated using this composition are as described supra. Moreover, the b-adrenergic receptor antagonist and the corticosteroid are as described supra. Preferably, in this method, the b-adrenergic receptor antagonist is administered in an amount of from about 1% to about 100% of the FDA approved doses of each agent to about and the corticosteroid is administered in an amount of from about 0.1% to about 100% of the FDA approved doses of each agent.

This invention provides for the use of the active beta-adrenergic receptor binding forms of beta-adrenergic antagonists with inverse agonist activity in the treatment of asthma, COPD, and other diseases that are marked by airway hyperresponsiveness, including, but not limited to, emphysema, Churg-Strauss syndrome, bronchitis, and bronchiectasis. The beta-adrenergic antagonists described herein can be in pure or substantially pure enantiomeric or diastereomeric form or can be racemic mixtures.

Especially preferred for use according to the invention are the beta-adrenergic antagonists: nadolol, e.g., as the hydrochloride: bupranolol, e.g., as the hydrochloride; butoxamine, e.g., as the hydrochloride; carazolol, e.g., as the hydrochloride; carvedilol; , e.g., as the hydrochloride; ICI-118,551, i.e., as the hydrochloride; levobunolol, e.g., as the hydrochloride; metoprolol, as the tartrate or succinate; propranolol, e.g., as the hydrochloride; sotalol, e.g., as the hydrochloride; timolol; e.g., as the hydrochloride; and the salts, solvates, analogues, congeners, bioisosteres, hydrolysis products, metabolites, precursors, and prodrugs thereof. Particularly preferred antagonists are carvedilol and nadolol. A most particularly preferred beta-antagonist with inverse agonist activity is nadolol. As used herein, the recitation of an antagonist compound, or, where appropriate, an agonist compound, includes all pharmaceutically acceptable salts of those compounds unless excluded. Thus, the recitation of nadolol as the hydrochloride does not exclude other pharmaceutically acceptable salts that have been prepared or that can be prepared.

In the case of salts, it is well known that organic compounds, including compounds having activities suitable for methods according to the present invention, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound or analogue includes such salt forms as occur at physiological pH or at the pH of a pharmaceutical composition unless specifically excluded.

Similarly, prodrug esters can be formed by reaction of either a carboxyl or a hydroxyl group on compounds or analogues suitable for methods according to the present invention with either an acid or an alcohol to form an ester. Typically, the acid or alcohol includes a lower alkyl group such as methyl, ethyl, propyl, isopropyl, butyl, isobutyl, and tertiary butyl. These groups can be substituted with substituents such as hydroxy, or other substituents. Such prodrugs are well known in the art and need not be described further here. The prodrug is converted into the active compound by hydrolysis of the ester linkage, typically by intracellular enzymes. Other suitable groups that can be used to form prodrug esters are well known in the art. For example prodrugs can include amides prepared by reaction of the parent acid compound with a suitable amine. In some cases it is desirable to prepare double ester type prodrugs such as (acyloxy)alkyl esters or ((alkoxycarbonyl)oxy)alkyl esters. Suitable esters as prodrugs include, but are not necessarily limited to, methyl, ethyl, propyl, isopropyl, n-butyl, isobutyl, tert-butyl, morpholinoethyl, and N,N-diethylglycolamido. Methyl ester prodrugs may be prepared by reaction of the acid form of a compound having a suitable carboxylic acid group in a medium such as methanol with an acid or base esterification catalyst (e.g., NaOH, $H_2SO_4$). Ethyl ester prodrugs are prepared in similar fashion using ethanol in place of methanol. Morpholinylethyl ester prodrugs may be prepared by reaction of the sodium salt of a suitable compound (in a medium such as dimethylformamide) with 4-(2-chloroethyl)morphine hydrochloride (available from Aldrich Chemical Co., Milwaukee, Wis. USA.

Pharmaceutically acceptable salts include acid salts such as hydrochloride, hydrobromide, hydroiodide, sulfate, phosphate, fumarate, maleate, acetates, citrates, lactates, tartrates, sulfamates, malonate, succinate, tartrate, methanesulfonates, ethanesulfonates, benzenesulfonates, p-toluenesulfonates, cyclohexylsulfamates, quinates, formates, cinnamates, picrates, and other suitable salts. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts also include salts with bases such as alkali metal salts such as sodium or potassium, as well as pyridine salts, ammonium salts, piperazine salts, diethylamine salts, nicotinamide salts, calcium salts, magnesium salts, zinc salts, lithium salts, methylamino salts, triethylamino salts, dimethylamino salts, and tris(hydroxymethyl)aminomethane salts.

The subject to be treated can be a human patient or a socially or economically important animal, including, but not limited to, a dog, a cat, a horse, a sheep, a goat, or a pig. Methods according to the present invention are not limited to the treatment of humans.

Typically, the method of administration of the beta-adrenergic inverse agonist results in continuous levels of the beta-adrenergic inverse agonist in the bloodstream of the subject. Typically, the method exerts a therapeutic effect that is an upregulation of pulmonary beta-adrenergic receptors. Typically, the method exerts a therapeutic effect that is increased pulmonary airway relaxation responsiveness to beta.sub.2-adrenergic agonist drugs. This provides for combination therapy, discussed in detail below.

The beta-adrenergic inverse agonist can be administered in conjunction with one or more pharmaceutical excipients. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. The beta-adrenergic inverse agonist can be administered in conjunction with one or more pharmaceutically acceptable carriers. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agent, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, especially as described below under combination therapy. For administration of any of the compounds used in the present invention, preparations should meet sterility, pyrogenicity, general safety, and purity standards as required by the FDA Office of Biologics Standards or by other regulatory organizations regulating drugs.

Thus, the beta-adrenergic inverse agonist can be formulated for oral, sustained-release oral, buccal, sublingual, inhalation, insufflation, or parenteral administration. If the beta-adrenergic inverse agonist is administered orally, either in a conventional or a sustained-release preparation, it is typically administered in a conventional unit dosage form such as a tablet, a capsule, a pill, a troche, a wafer, a powder, or a liquid such as a solution, a suspension, a tincture, or a syrup. Oral formulations typically include such normally employed excipients as, for example, pharmaceutical grades of mannitol, lactose, starch, magnesium stearate, sodium saccharin, cellulose, magnesium carbonate, and other conventional pharmaceutical excipients. In certain defined embodiments, oral pharmaceutical compositions will comprise an inert diluent and/or assimilable edible carrier, and/or they may be enclosed in hard or soft shell gelatin capsules. Alternatively, they may be compressed into tablets. As another alternative, particularly for veterinary practice, they can be incorporated directly into food. For oral therapeutic administration, they can be incorporated with excipients or used in the form of ingestible tablets, buccal tablets, dragees, pills, troches, capsules, wafers, or other conventional dosage forms.

The tablets, pills, troches, capsules, wafers, or other conventional dosage forms can also contain the following: a binder, such as gum tragacanth, acacia, cornstarch, sorbitol, mucilage of starch, polyvinylpyrrolidone, or gelatin; excipients or fillers such as dicalcium phosphate, lactose, microcrystalline cellulose, or sugar; a disintegrating agent such as potato starch, croscarmellose sodium, or sodium starch glycolate, or alginic acid; a lubricant such as magnesium stearate, stearic acid, talc, polyethylene glycol, or silica; a sweetening agent, such as sucrose, lactose, or saccharin; a wetting agent such as sodium lauryl sulfate; or a flavoring agent, such as peppermint, oil of wintergreen, orange flavoring, or cherry flavoring.

When the dosage unit form is a capsule, it can contain, in addition to materials of the above types, a liquid carrier. Various other materials can be present as coatings or to otherwise modify the physical form and properties of the dosage unit. For instance, tablets, pills, or capsules can be coated with shellac, sugar, or both. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In one alternative, a sustained-release formulation is used. Sustained-release formulations are well-known in the art. For example, they can include the use of polysaccharides such as xanthan gum and locust bean gum in conjunction with carriers such as dimethylsiloxane, silicic acid, a mixture of mannans and galactans, xanthans, and micronized seaweed, as recited in U.S. Pat. No. 6,039,980 to Baichwal. Other sustained-release formulations incorporate a biodegradable polymer, such as the lactic acid-glycolic acid polymer recited in U.S. Pat. No. 6,740,634 to Saikawa et al. Still other sustained-release formulations incorporate an expandable lattice that includes a polymer based on polyvinyl alcohol and polyethylene glycol, as recited in U.S. Pat. No. 4,428,926 to Keith. Still other sustained-release formulations are based on the Eudragit™ polymers of Rohm & Haas, that include copolymers of acrylate and methacrylates with quaternary ammonium groups as functional groups as well as ethylacrylate methylmethacrylate copolymers with a neutral ester group. A particularly-preferred extended release composition suitable for use in methods according to the present invention is an extended-release composition that contains nadolol as its active ingredient.

Oral liquid preparations can be in the form of, for example, aqueous or oily suspensions, solutions, emulsions, syrups, tinctures, or elixirs, or can be presented as a dry product for reconstitution with water or other suitable vehicles before use. Such liquid preparations can contain conventional additives such as suspending agents, for example, sorbitol syrup, methylcellulose, glucose/sugar syrup, gelatin, hydroxymethylcellulose, carboxymethylcellulose, aluminum stearate gel, or hydrogenated edible fats; emulsifying agents, such as lecithin, sorbitan monooleate, or acacia; non-aqueous vehicles (which may include edible oils), for example, almond oil, fractionated coconut oil, oily esters, propylene glycol, or ethyl alcohol; or preservatives, for example, methylparaben, propylparaben, or sorbic acid. The preparations can also contain buffer salts, flavoring, coloring, or sweetening agents, e.g., mannitol, as appropriate.

One skilled in the art recognizes that the route of administration is an important determinant of the rate of efficiency of absorption. For example, the alimentary route, e.g., oral, rectal, sublingual, or buccal, is generally considered the safest route of administration. The delivery of the drugs into the circulation is slow, thus eliminating rapid high blood levels of the drugs that could potentially have adverse acute effects. Although this is considered the safest route of administration, there are several disadvantages. One important disadvantage is that the rate of absorption varies, which is a significant problem if a small range in blood levels separates a drug's desired therapeutic effect from its toxic effect, i.e., if the drug has a relatively low therapeutic index. Also, patient compliance is not always ensured, especially if the rectal route of administration is chosen or if oral administration is perceived by the patient as unpleasant.

Furthermore, with oral administration, extensive hepatic metabolism can occur before the drug reaches its target site. Another route of administration is parenteral, which bypasses the alimentary tract. One important advantage of parenteral administration is that the time for the drug to reach its target site is decreased, resulting in a rapid response, which is essential in an emergency.

Furthermore, parenteral administration allows for delivery of a more accurate dose. Parenteral administration also allows for more rapid absorption of the drug, which can result in increased adverse effects. Unlike alimentary administration, parenteral administration requires a sterile formulation of the drug and aseptic techniques are essential. The most significant disadvantage to parenteral administration is that it is not suitable for insoluble substances. In addition to alimentary and parenteral administration routes, topical and inhalation administrations can be useful. Topical administration of a drug is useful for treatment of local conditions; however, there is usually little systemic absorption. Inhalation of a drug provides rapid access to the circulation and is the common route of administration for gaseous and volatile drugs, or drugs that can be vaporized or nebulized. It is also a desired route of administration when the targets for the drug are present in the pulmonary system.

When compounds are formulated for parenteral administration, e.g., formulated for injection via the intravenous, intramuscular, subcutaneous, intralesional, or intraperitoneal routes, many options are possible. The preparation of an aqueous composition that contains an effective amount of the beta-adrenergic inverse agonist as an active ingredient will be known to those of skill in the art. Typically, such compositions can be prepared as injectables, either as liquid solutions and/or suspensions. Solid forms suitable for use to prepare solutions and/or suspensions upon the addition of a liquid prior to injection can also be prepared. The preparations can also be emulsified.

The pharmaceutical forms suitable for injectable use include sterile aqueous solutions and/or dispersions; formulations including sesame oil, peanut oil, synthetic fatty acid esters such as ethyl oleate, triglycerides, and/or aqueous propylene glycol; and/or sterile powders for the extemporaneous preparation of sterile injectable solutions and/or dispersions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. In all cases the form must be sterile and/or must be fluid to the extent that the solution will pass readily through a syringe and needle of suitable diameter for administration. It must be stable under the conditions of manufacture and storage and must be preserved against the contaminating action of microorganisms, such as bacteria or fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and use, these preparations contain a preservative to prevent the growth of microorganisms. Suitable non-sensitizing and non-allergenic preservatives are well known in the art.

The carrier can also be a solvent and/or dispersion medium containing, for example, water, ethanol, a polyol (for example, glycerol, propylene glycol, and/or liquid polyethylene glycol, and/or the like), suitable mixtures thereof, and/or vegetable oils. The proper fluidity can be maintained for example, by the use of a coating, such as lecithin, by the maintenance of a suitable particle size in the case of a dispersion, and/or by the use of surfactants. The prevention of the action of microorganisms can be brought about by the inclusion of various antibacterial and/or antifungal agents, for example, parabens, chlorobutanol, phenol, sorbic acid, or thimerosal. In many cases it will be preferable to include isotonic agents, for example, sugars or sodium chloride. In many cases, it is preferable to prepare the solution in physiologically compatible buffers such as Hanks's solution, Ringer's solution, or physiological saline buffer. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by sterilization. Sterilization is typically performed by filtration. Generally, dispersions are prepared by incorporating the various sterilized active ingredients into a sterile vehicle which contains the basic dispersion medium and/or the other required ingredients. In the case of sterile powders for the preparation of sterile injectable solutions, the preferred methods of preparation are vacuum-drying and/or freeze-drying techniques that yield a powder of the active ingredients plus any additional desires ingredients from a previously sterile-filtered solution thereof. The preparation of more-concentrated or highly-concentration solutions for direct injection is also contemplated, where the use of dimethyl sulfoxide (DMSO) as solvent is envisioned to result in extremely rapid penetration, delivering high concentrations of the active agents to a small area if desired.

For parenteral administration in an aqueous solution, for example, the solution should be suitably buffered if necessary and/or the liquid diluent first rendered isotonic with sufficient saline, glucose, or other tonicity agent. These particular aqueous solutions are especially suitable for intravenous, intramuscular, subcutaneous, or intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected into the proposed site of infusion (see, e.g., "Remington's Pharmaceutical Sciences" (15.sup.th ed.), pp. 1035-1038, 1570-1580). Some variation in dosage will necessarily occur depending on the condition of the subject being treated. The person responsible for administration will, in any event, determine the appropriate dose for the individual subject. Compounds and compositions according to the invention can also be formulated for parenteral administration by bolus injection or continuous infusion and can be presented in unit dose form, for instance as ampoules, vials, small volume infusions, or pre-filled syringes, or in multi-dose containers with an added preservative.

Another route of administration of compositions according to the present invention is nasally, using dosage forms such as nasal solutions, nasal sprays, aerosols, or inhalants. Nasal solutions are usually aqueous solutions designed to be administered to the nasal passages in drops or sprays. Nasal solutions are typically prepared so that they are similar in many respects to nasal secretions, so that normal ciliary action is maintained. Thus, the aqueous nasal solutions usually are isotonic and/or slightly buffered in order to maintain a pH of from about 5.5 to about 6.5. In addition, antimicrobial preservatives, similar to those used in ophthalmic preparations, and/or appropriate drug stabilizers, if required, can be included in the formulation. Various commercial nasal preparations are known and can include, for example, antibiotics or antihistamines. Spray compositions can be formulated, for example, as aqueous solutions or suspensions or as aerosols delivered from pressurized packs, with the use of a suitable propellant, such as dichlorodifluoromethane, trichlorofluoromethane, dichlorotetrafluoroethane, 1,1,1,2,3,3,3-heptafluoropropane, 1,1,1,2-tetrafluoroethane, carbon dioxide, or other suitable gas.

Additional formulations that are suitable for other modes of administration include vaginal suppositories and/or pessaries. A rectal pessary or suppository can also be used. Suppositories are solid dosage forms of various weights or shapes, usually medicated, for insertion into the rectum, vagina, or urethra. After insertion, suppositories soften, melt, and/or dissolve into the cavity fluids. In general, for suppositories, traditional binders or carriers can include polyalkylene glycols, cocoa butter, or triglycerides.

Other dosage forms, including but not limited to liposomal formulations, ointments, creams, lotions, powders, or creams, can alternatively be used. Ointments and creams can, for example, be formulated with an aqueous or oily base with the addition of suitable gelling agents and/or solvents. Such bases, can thus, for example, include water and/or an oil such as liquid paraffin or a vegetable oil such as arachis (peanut) oil or castor oil or a solvent such as a polyethylene glycol. Thickening agents which can be used include soft paraffin, aluminum stearate, cetostearyl alcohol, polyethylene glycols, microcrystalline wax, and beeswax. Lotions can be formulated with an aqueous or oily base and will in general also contain one or emulsifying agents, stabilizing agents, dispersing agents, suspending agents, or thickening agents. Powders for external application can be formed with the aid of any suitable powder base, for example, talc, lactose, or starch.

Because of the nature of the interaction between beta-adrenergic antagonists with inverse agonist activity and the beta-adrenergic receptors with which they interact, the therapeutic response develops gradually over time as the receptor density in the affected tissues increases in response to the administration of inverse agonists. Therefore, in one particularly preferred alternative, the dosage is titrated at the start of administration with gradual increases. In other words, the beta-adrenergic antagonist is administered over time in a series of graduated doses starting with the lowest dose and increasing to the highest dose. When the highest dose is reached, the beta-adrenergic antagonist continues to be administered at that dose (the maintenance dose).

For example, with nadolol administered orally, treatment can begin with 1 mg dosages, then progress through 3 mg, 5 mg, 10 mg, 15 mg, and then to higher maintenance dosages such as 25 mg, 30 mg, 50 mg, 70 mg, 100 mg, or higher as deemed necessary, depending on the particular condition to be treated, the severity, and the response of the condition to the treatment. One particularly preferred dosage regimen begins at 10 mg, then progresses through 20 mg, 40 mg, 80 mg, 120 mg, and up to 160 mg based on defined dose escalation criteria determined by lung function, symptoms, heart rate, and blood pressure, as detailed further below. Analogous dosing regimens can be used with other inverse agonists, the exact starting dose typically depending on the affinity of the inverse agonist for the binding site of the beta-adrenergic receptor.

Depending on the specific conditions being treated, such agents may be formulated and administered systemically or locally. Typically, administration is systemic. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. Typically, oral administration is preferred.

For injection, the agents of the invention may be formulated in aqueous solutions. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Typically, in methods according to the present invention, the inverse agonist is administered in a daily dose or multiple times per day, depending on the half-life of the inverse agonist. Alternatively, the inverse agonist can be administered less frequently, such as every other day, every third day, every fourth day, every week, and the like. Less frequent dosing may be achieved by the development of a depot of the drug in the body resulting in release of the drug over a sustained time period. This depot may be oral or injected. One skilled in the art of pharmacokinetics will recognize the importance of understanding the bioavailability and the half-life of a drug in relation to dosing of the particular drug. It is well known that a drug accumulates in the body if the time interval between doses is less than four of its half-lives, in which case, the total body stores of the drug are increased exponentially to a plateau or steady-state concentration. The average total body store of a drug at the plateau is a function of the dose, the interval between doses, the bioavailability of the drug, and the rate of the elimination of the drug. Thus, one of ordinary skill in the art is capable of determining the dose and interval of the dose for a given drug to achieve the desired effect.

Another embodiment of the present invention is methods and compositions that incorporate multiple-drug or combination therapy for the treatment of pulmonary airway diseases. Patients with pulmonary airway diseases often are prescribed multiple drugs that work in combination to control their symptoms. Nevertheless, it is nonobvious as to which drugs will work in combination as drugs may interact in a subtractive manner and reduce the other's efficacy. Alternatively, a drug may alter another drug's pharmacokinetic properties so as to require dosage adjustment or may result in toxic side effects such as observed by drugs that are modified by hepatic modification enzymes such as cytochrome P450s. There may be no difference in therapeutic effect upon administration of another drug which could be due to a similar mode of action or lack of combinatorial effect. More preferably drug combinations would be additive or even more preferred synergistic to such a level that drug levels may be reduced to lower potential side effects of one or more of the drugs which are more problematic at higher levels. Based on these issues, it is nonobvious that drug combinations and drug combination dosing regimes and dose levels.

Preferably, the allergen-induced airway hyper responsiveness and the allergen-induced increase in mucus-containing cells are decreased after administration of said b-adrenergic receptor antagonist and a corticosteroid. Similarly, it is preferable that airway eosinophilia is reduced after administration of said b-adrenergic receptor antagonist and a corticosteroid. Moreover, it is preferable that levels of TGFb1 and TNFa are reduced after administration of said b-adrenergic receptor antagonist and a corticosteroid.

Glucocorticosteroids are very effective in ameliorating symptoms and preventing exacerbations in most asthma patients. However, asthma remains poorly controlled in some patients despite high dose inhaled or systemic steroids (18), and the rate of steroid-induced side effects increase as the dose increases (16-17). Chronic treatment with a subset of beta-blockers, i.e., those possessing $\beta2$-AR inverse agonist properties, reduces airway hyperresponsiveness, inflammatory cell numbers in bronchoalveolar lavage fluid, and epithelial mucous metaplasia in allergen-driven murine asthma models (19-20, 23-24). The relevance of these beneficial effects to human subjects is suggested by the observed reduction in airway hyperresponsiveness in two proof-of-concept trials administering nadolol to mild asthmatics using a dose escalation protocol (21-22). A $\beta$-blocker without inverse agonism activity did not produce the reductions in airway hyperresponsiveness or inflammation (20, 24).

However, the interaction of co-treatment with $\beta2$-AR inverse agonists and glucocorticosteroids in asthma or asthma models has not been investigated. Since both glucocorticosteroids and $\beta2$-AR inverse agonists exhibit anti-inflammatory properties in asthma models, these drugs could interact additively, greater than additively (synergistically), or less than additively. This is an important question for at least two reasons. First, glucocorticosteroids are an essential component of all stages of chronic asthma treatment. Therefore, any treatment that interferes with the therapeutic effect of this class of drugs is likely to be of limited utility. Secondly, despite their usefulness, glucocorticosteroids have serious side effects that are often dose-dependent. Therefore there is a real need to develop anti-inflammatory therapies that will allow a reduction in the glucocorticosteroid dose without a loss in their therapeutic efficacy. In general, treatment with the $\beta2$-AR antagonist nadolol additively enhanced the anti-inflammatory activity of intermediate-dose dexamethasone as measured by reductions in BAL eosinophilia, mucin volume density, and Type 2 cytokines.

The results of the reductions in BAL eosinophilia and mucin volume density are very clear and strongly suggestive of an additive effect between the glucocorticosteroid and $\beta2$-AR antagonist. Importantly, this additive effect was equivalent to, or greater than, that produced using a 10-fold higher dose of dexamethasone in the murine model of asthma. These results also showed that, at least for the additive effect of nadolol and dexamethasone on reducing eosinophilia and mucin volume, the additive effect was observed irrespective of whether combinations of intermediate or low doses of nadolol and dexamethasone were used.

These results suggest addition of a $\beta2$-AR antagonist with inverse agonist activity to a glucocorticosteroid may be appropriate when steroids alone do not control the disease, or if a decrease in the steroid dose is desired due to the dose-dependence of the adverse effect. These results are especially encouraging for this latter indication because of the magnitude of the observed 'glucocorticoid-sparing' effect produced by the $\beta2$-AR antagonist, nadolol. At both, reducing BAL eosinophilia, and mucin volume, addition of nadolol allowed a full log unit reduction of the dexamethasone dose with no loss of efficacy at either anti-inflammatory response.

The effect of the combination of nadolol and dexamethasone producing a general lowering of Th2 cytokines in BAL fluid was more tenuous. While this finding would be expected in the model of allergic lung inflammation, the rise in Th2 cytokines was not as dramatic as the increase in eosinophils, or mucin volume. A likely reason for the decreased response is that peak levels of most cytokines occurs 4-8 h after challenge while these measurements were made at 24 h. Also, unlike the eosinophil counts and the mucin volume measurements, the cytokine levels were measured after only a single concentration of nadolol (250 ppm), or dexamethasone (4.0 mg/kg/day), or after administration of a single combination of nadolol (25 ppm) and dexamethasone (0.4 mg/kg/day). Nevertheless, these experiments still yielded significant differences in BAL cytokines from previous OVA S/C experiments (19).

Based on the present invention, there at least two lines of evidence suggest that the anti-inflammatory mechanisms of action may be different between dexamethasone and nadolol. One is that dexamethasone is more effective than nadolol at reducing eosinophils in BAL, but nadolol is more effective than dexamethasone at reducing epithelial mucin content. If the mechanisms of action of these two compounds were the same, one would expect their maximal effects would be at the same therapeutic endpoint. Second, the time course for the onset of action differs between nadolol and dexamethasone is different. In a previous study, 7 days of treatment with nadolol produced a very modest reduction in mucin content while 28 days resulted in an almost 90% reduction (19). On the other hand, glucocorticosteroids can produce a therapeutic effect within hours, and in a murine asthma model maximal effects can be observed within 5 days (25).

Taken together, these results suggest that treatment with nadolol may be 'glucocorticoid-sparing' by allowing a reduction in the steroid dose with no loss of therapeutic effectiveness. Further evidence that this is an important desired effect is evidenced by the fact that an FDA-approved drug, omalizumab, has shown this desirable effect in a clinical trial designed to test the ability of the drug to reduce the steroid dose needed to prevent exacerbations (29). If clinical studies show the same effects that we have observed in the murine model, nadolol could become an adjunct therapy to glucocorticosteroids.

Figure 2:
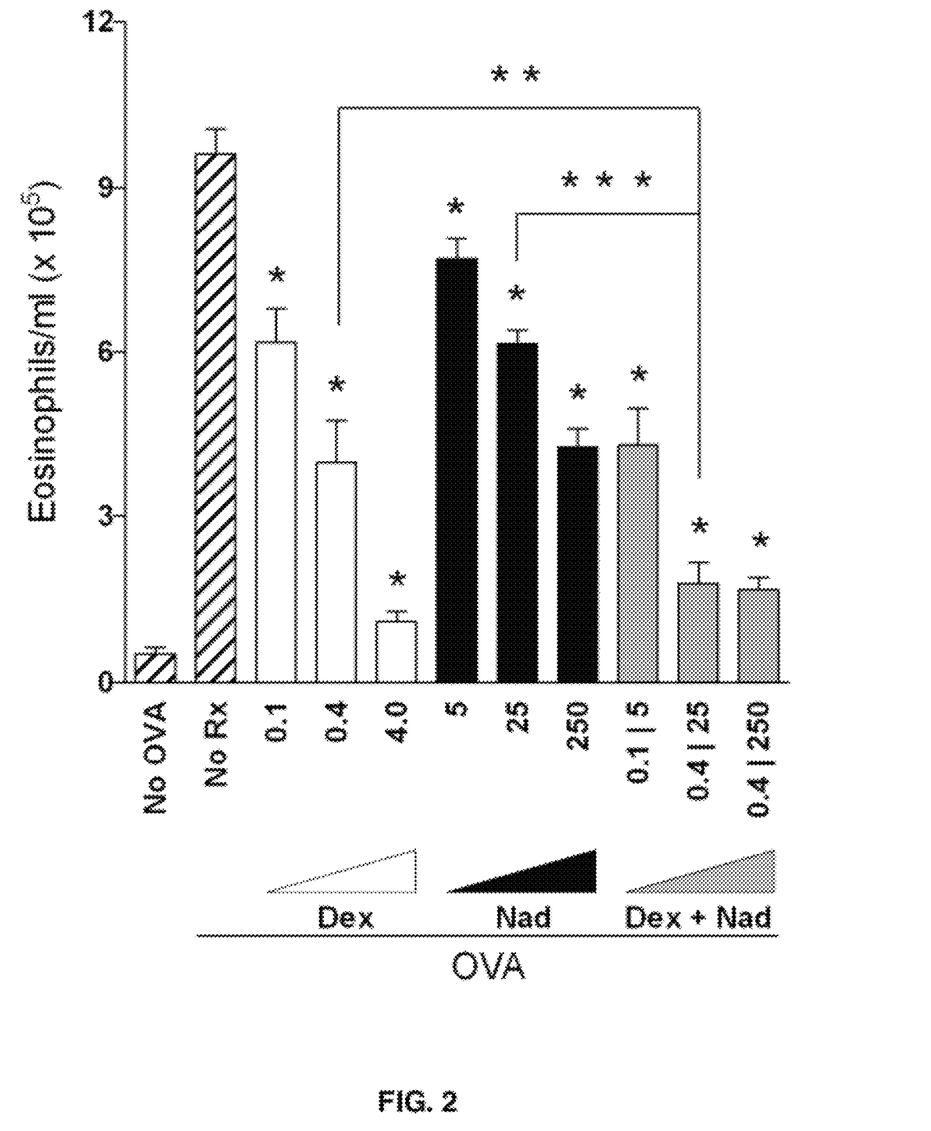
FIG. 2 illustrates the effects of dexamethasone and nadolol on BAL eosinophils. Eosinophil numbers in BAL collected from control mice (No OVA), OVA immunized mice administered vehicle (No Rx), dexamethasone (black), the $β_2$-AR nadolol (white), or a combination dose of dexamethasone and nadolol (stripes). BAL was collected 24 hours after the last challenge. Values are the means±SEM of data from 4 to 5 mice in each group (n=4-5). *, indicate significant difference compared to No Rx, P<0.05; , indicate significant difference compared to 0.4 mg/kg/day dexamethasone treatment, P<0.05; *, and indicate significant difference compared to 25 ppm nadolol treatment, P<0.05.

Particularly, one preferred embodiment of the present invention discloses that the simultaneous administration (or co-administration) of dexamethasone and nadolol reduces airway eosinophilia. Airway eosinophil numbers in BAL are significantly increased in untreated mice that have been sensitized and challenged (S/C) with OVA, as illustrated in FIG. 2. The administration of various concentrations of dexamethasone alone produces a dose-dependent reduction in eosinophils. The administration of the inverse β-agonist nadolol (23) alone also markedly reduces eosinophils in BAL. However, the co-administration of low-dose of nadolol (25 ppm) and low-dose of dexamethasone (0.4 mg/kg/day) yield significantly greater reductions in eosinophils than either drug given alone. In fact, the resulting additive effect of co-administration is equivalent to administrating a 10-fold higher (4 mg/kg/day, 8 days) dose of dexamethasone alone. Another preferred embodiment of the present invention discloses that the simultaneous administration of dexamethasone and nadolol reduces the levels of Type 2 cytokines.

Vehicle treated OVA S/C mice (No Rx) have elevated levels of eotaxin, MDC, TARC, IL-5, IL-13, TGFβ1 and TNFα in BALF compared with untreated control mice. Consistent with the changes in cellular inflammation, the co-administration of low-dose (25 ppm) nadolol with low-dose dexamethasone (0.4 mg/kg) results in a reduction in the levels of the Type 2 cytokines, eotaxin, MDC, TARC, IL-5, and IL-13), comparable to the reductions produced by high-dose (4.0 mg/kg) dexamethasone. For IL-1α, high dose dexamethasone produces a significant increase, while high dose nadolol (250 ppm) lowers it to level comparable to the vehicle treated group (No Rx). The IL-23 levels are unaffected except that high dose nadolol have lower levels than either high dose dexamethasone or the co-administration of low dose nadolol and low dose dexamethasone. For IL-12p70 high dose nadolol results in reduced levels compared to the co-administration of low dose nadolol and low dose dexamethasone. While for TNFα, high dose nadolol produces an increase compared to the levels in high dose dexamethasone treated mice, and for eotaxin high dose nadolol produces higher levels than either high dose dexamethasone, or the co-administration of low dose nadolol and low dose dexamethasone. There is no effect by any of the treatments in the remaining cytokines (IL-6, IL-17, and IFNγ).

Another preferred embodiment of the present invention discloses that the simultaneous administration of beta-adrenergic antagonists with inverse agonist activity (or beta-blockers) such as nadolol in combination with corticosteroids such as dexamethasone attenuates the volume density of epithelial mucin. To determine whether the simultaneous administration of dexamethasone and nadolol additively reduces epithelial mucin content to a greater extent than either drug given alone, sections from the axial bronchi of experimental mice are assessed by means of PAFS staining. Minimal intracellular mucin are observed in control mice that have not been sensitized and challenged with OVA, whereas in mice that have undergone sensitization and challenge, there is increased mucin content and airway epithelial cell height (mucous metaplasia). Within the OVA S/C group, the chronic administration of dexamethasone (4 mg/kg/day) decreases mucin content and partially reverses the changes in airway epithelial cell morphology. However, the effect is less pronounced when high-dose nadolol (250 ppm) is used, which produces an effect that is comparable to mice that have been treated with a combination of low-dose dexamethasone (0.4 mg/kg/day) and low-dose nadolol (25 ppm). Furthermore, the combined therapeutic regimen of low-dose of both dexamethasone and nadolol yield greater reductions in mucin content than either of these drugs given alone at low doses, indicative of additive effect.

Another preferred embodiment of the present invention discloses the effect of nadolol over time on the suppression of airway eosinophilia and mucin volume density after completion of the sensitization process. In previous experiments, a delay in the onset of action of β-blockers on the asthma phenotype and a temporal separation in effect on different parameters of inflammation was observed (19, 20). These results obtained herein are comparable to a previous study that showed maximal reductions in AHR after 7 days of treatment (26). Maximal reductions in airway eosinophilia and significant reductions in mucin volume from OVA S/C are detected at day 7 (~50%) compared to control.

The results disclosed herein demonstrate the benefits of simultaneously co-administrating beta-adrenergic antagonists with inverse agonist activity and glucocorticosteroids to significantly reduce the undesirable side-effects associated with the treatment of asthma (as currently practiced, that is when glucocorticosteroids are used alone), while enhancing the performance of the treatment. While glucocorticosteroids are very effective in ameliorating symptoms and preventing exacerbations in most asthma patients (6, 7), asthma remains poorly controlled in some patients despite high dose inhaled or systemic steroids (6, 7), and the rate of steroid-induced side effects increase as the dose increases (6, 7).

Chronic treatment with a subset of β-blockers (those possessing $β_2$-AR inverse agonist properties) reduces airway hyperresponsiveness (AHR), inflammatory cell numbers in bronchoalveolar lavage (BAL) fluid, and epithelial mucous metaplasia (19, 20, 26, 27). The relevance of such beneficial effects to human subjects is suggested by the observed reduction in AHR in two proof-of-concept trials in mild asthmatics (21, 22). However, the interaction of co-treatment with β-blockers and glucocorticosteroids in asthma or asthma models had not been investigated so far and the present invention teaches the benefits of their co-administration.

Since both glucocorticosteroids and β-blockers exhibit anti-inflammatory properties in asthma models; in principle, these drugs could interact additively, greater than additively (synergistically), or less than additively. The present invention demonstrates that treatment with a β-blocker, nadolol, additively enhances the anti-inflammatory activity of low-dose dexamethasone as measured by reductions in BAL eosinophilia, Type 2 cytokines, and mucin volume density. Importantly, this additive effect is equivalent to, or greater than that produced using a 10-fold higher dose of dexamethasone in a murine model of asthma. Therefore, the cost-to-benefit ratio of anti-inflammatory therapy may favor addition of a β-blocker to a glucocorticosteroid, and particularly in cases where the disease is not controlled by a low-dose steroid alone.

While the invention described herein specifically relates to the co-administration of beta-adrenergic antagonists with inverse agonist activity and steroids to enhance the treatment for asthma, one of ordinary skills in the art, with the benefit of this disclosure, would recognize the extension of this approach for the treatment of other inflammatory diseases.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Animals

Six-week to eight-week-old BALB/c mice (Jackson Animal Laboratory, Bar Harbor, Me.) were housed under specific pathogen-free conditions.

EXAMPLE 2

Animal Sensitization and Challenge

Mice were immunized against allergen by means of sensitization (once weekly intraperitoneal injection on days 0, 7, and 14) and challenge (once daily intranasal instillation for 5 days on days 41-45) with ovalbumin (OVA) as described (FIG. 1) (19).

EXAMPLE 3

Drug Administration

Figure 1:
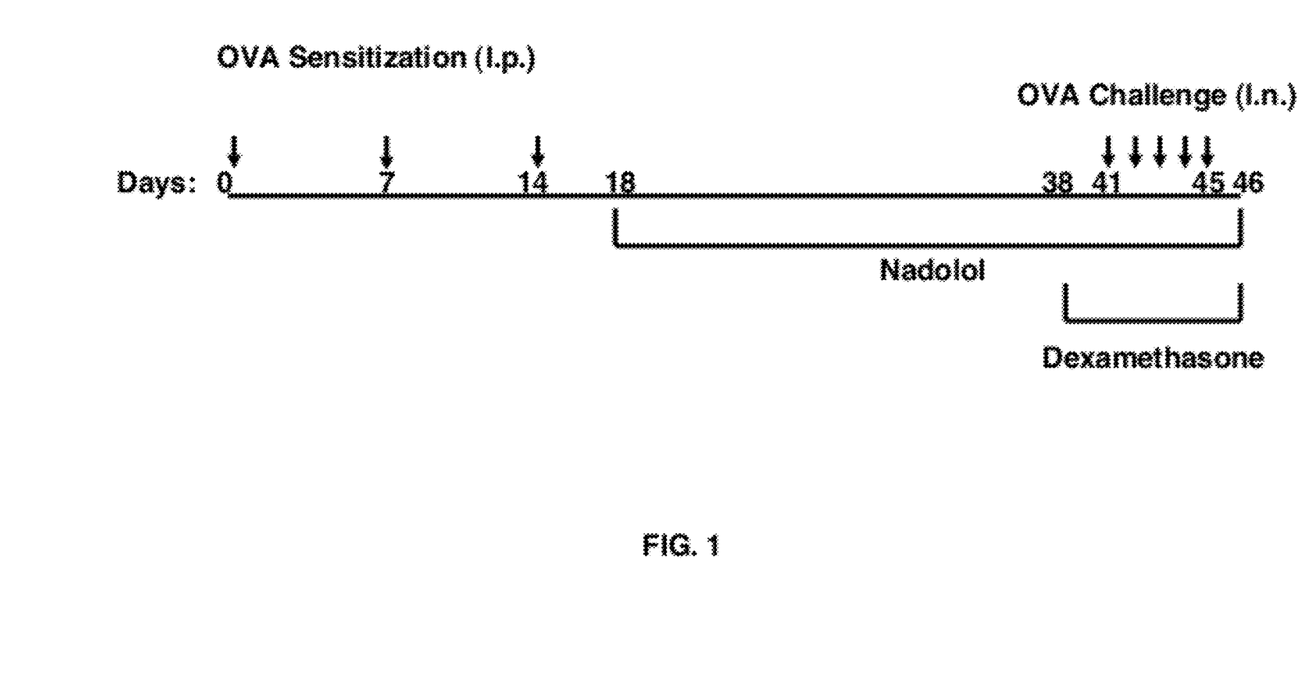
FIG. 1 is a schematic diagram illustrating the protocol for ovalbumin (OVA) sensitization, challenge, and drug administration.

A group of mice were fed (ad libitum) mouse chow containing nadolol (Sigma, St. Louis, Mo.) (23), after the OVA sensitization process was completed on days 18-45 (28 day treatment) at a concentration of 250, 25, or 5 ppm. The pharmacokinetic profile of nadolol made the drug suitable for dosing orally in the chow (19). Nadolol, a non-selective β-blocker for $β_1$- and $β_2$-AR, was selected because it is a full inverse agonist at the $β_2$-AR (23, 24). Dexamethasone, a potent synthetic glucocorticosteroid, was administered via intraperitoneal injection (IP) alone or in addition to nadolol on days 38-45 (8 days) at a concentration of 4, 0.4, or 0.1 mg/kg/day (FIG. 1). Untreated sensitized and challenged mice or mice that had not undergone the sensitization and challenge process, received vehicle and were fed with normal mouse chow. To determine the onset of nadolol action, a group of mice began treatment for various times with nadolol (250 ppm) after completion of the sensitization process. Experimental mice were sacrificed on day 46.

EXAMPLE 4

Bronchoalveolar Lavage

Brochoalveolar lavage (BAL) fluid was acquired via infusion and recovery of cold PBS (2×1 ml) through the tracheal cannula from euthanized (pentobarbital 0.1 ml of 65 mg/ml) mice. Brochoalveolar lavage total leukocyte count and differentiated cell counts were performed as described (19).

EXAMPLE 5

Histochemistry

Lungs were perfused with 4% paraformaldehyde in PBS (pH 7.0) via a tracheal cannula at room temperature, then removed from the thoracic cavity and further fixed overnight at 4° C. (25). After overnight fixation, lungs were embedded in paraffin and then sectioned and stained with periodic acid fluorescent Schiff's (PAFS) reagent to examine intracellular mucin. Tissue sections were examined under a 40× objective and images (MagnaFire 2.1 Optronics) were acquired prior to any measurements and analyzed (ImagePro Plus) by blinded investigators (25).

EXAMPLE 6

Cytokines

The supernatants from brochoalveolar lavage samples, collected 24 hours after the last challenge with OVA, were provided to Pierce Searchlight, Aushon BioSystems, Inc. in blinded fashion. The concentrations of eotaxin, macrophage-derived chemokine (MDC), thymus and activation regulated chemokine (TARC), interleukin (IL)-1α, IL-5, IL-6, IL-12p70, IL-13, IL-17, IL-23, interferon (IFN), tumor necrosis factor alpha (TNF-a) and transforming growth factor beta (TGF-β1) were measured using multiplex enzyme-linked immunosorbent assay.

EXAMPLE 7

Statistical Analysis

Statistical analysis for multiple groups was performed using one-way analysis of variance followed by Dunnett's multi-comparison test (Prism, GraphPad software, San Diego, Calif.). Quantitative data are presented as mean±standard error of the mean (SEM; expressed as the percent standard error of the mean). P<0.05 was considered statistically significant.

EXAMPLE 8

Administration of Dexamethasone and Nadolol Individually, or in Combination, Reduces Airway Eosinophilia Leukocytes and cytokines were measured in BAL fluid of OVA-sensitized mice 24 hours after the last of five daily nasal challenges with OVA (FIG. 1). As illustrated in FIG. 2, airway eosinophil numbers were markedly increased in mice not treated with anti-inflammatory drugs. Administration of various concentrations of dexamethasone or nadolol, alone or in combination, both produced dose-dependent reductions in eosinophils. However, co-administration of both drugs together at low (dexamethasone 0.1 mg, nadolol 5 ppm), or intermediate (dexamethasone 0.4 mg, nadolol 25 ppm) concentrations yielded significantly greater reductions in eosinophils than either drug given alone.

Furthermore, as shown in FIG. 2, the effect of co-administration of the two drugs at these concentrations was approximately additive. At low doses, the reduction in eosinophils with dexamethasone alone was 36%, with nadolol alone was 20%, and with both together was 55%. At intermediate doses, the reduction in eosinophils with dexamethasone alone was 58%, with nadolol alone was 36%, and with both together was 81%. High-dose dexamethasone (4 mg) was substantially more effective in suppressing eosinophilic inflammation than high-dose nadolol (250 ppm, $P<0.05$, FIG. 2B), as observed previously (Nguyen et al., 2008). However, the co-administration of intermediate-dose dexamethasone and nadolol was just as effective as high-dose (4.0 mg) dexamethasone (81% and 89% reduction in eosinophils respectively). There was no additional benefit from increasing the nadolol dose 10-fold when co-administered with intermediate dose dexamethasone (81% reduction in eosinophils with nadolol 25 ppm versus 83% with nadolol 250 ppm, $P<0.05$), indicating a plateau of effect under these conditions (FIG. 2).

Thus at low and intermediate doses, administration of the combination of dexamethasone and nadolol resulted in an additive anti-inflammatory effect. For example, co-administration of the intermediate dose of dexamethasone (0.4 mg/kg/day) with the intermediate dose of nadolol (25 ppm), produced a reduction in BAL eosinophil numbers comparable to that observed by sole administration of dexamethasone at a 10-fold higher dose.

EXAMPLE 9

Figure 3A:
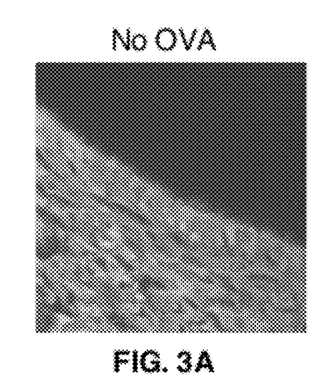
FIGS. 3A-3F illustrate the effects of dexamethasone and nadolol on mucin content in the airway epithelium. Mucin content was measured using periodic acid fluorescent Schiff staining of lung tissue from control mice (No OVA.
Figure 3B:
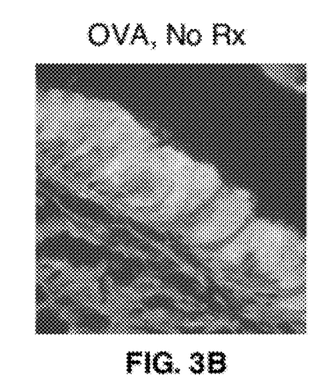
Figure 3C:
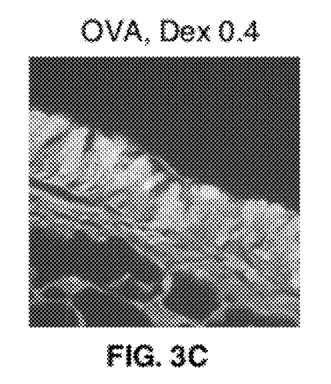
Figure 3D:
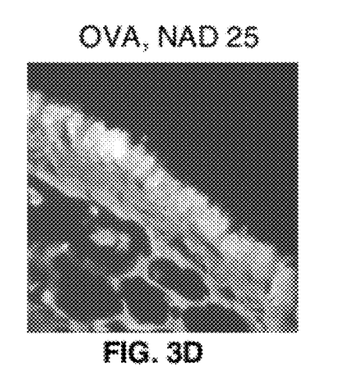
Figure 3E:
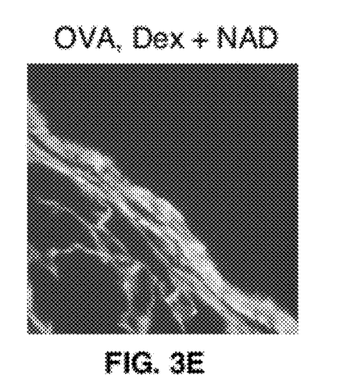

Administration of Dexamethasone and Nadolol Individually, or in Combination, Reduces Airway Epithelial Cell Mucin Content To determine whether the combined administration of dexamethasone and nadolol additively reduces epithelial mucin content to a greater extent than either drug given alone, (as was seen with airway eosinophilia), sections from the axial bronchi of experimental mice were assessed by means of PAFS staining. Minimal intracellular mucin was observed in control mice (FIG. 3A) that had not been sensitized and challenged with OVA, whereas in mice that had undergone OVA S/C FIGS. 3B-3E, as was the case with BAL eosinophil numbers, there was a marked increase in mucin content and increased airway epithelial cell height (mucous metaplasia).

Figure 3F:
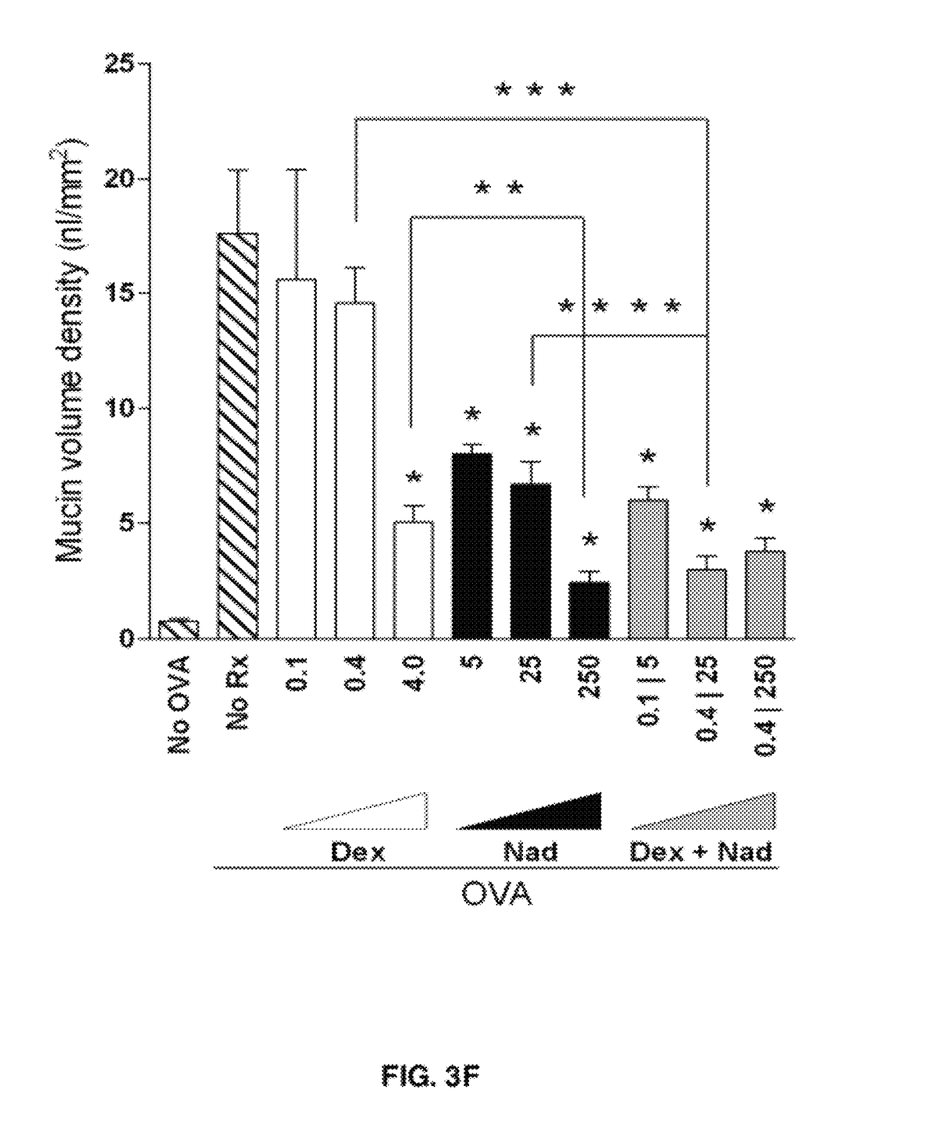

However, unlike nadolol's effect on eosinophilia, within the OVA S/C group, chronic administration of only high-dose high dose dexamethasone significantly decreased mucin content (FIG. 3F). Also, the effect (72%) was less in extent than with the use of high-dose nadolol (86% $P<0.05$). Again, unlike low- and intermediate-dose dexamethasone, all doses of chronic nadolol administration produced significant decreases in mucin content. As observed for BAL eosinophils numbers (FIG. 2), the combined therapeutic regimen of intermediate-dose dexamethasone and nadolol yielded greater reductions in mucin content than either of these drugs given alone, indicative of an additive effect, and produced a reduction in mucin content comparable to that produced by high-dose nadolol (83% and 86% reductions with the combination, and high-dose nadolol, respectively). Similarly, addition of intermediate dose nadolol to the intermediate dose of dexamethasone produced a reduction in mucin volume comparable to the decrease produced by a log unit higher dose of dexamethasone alone.

EXAMPLE 10

Time-Dependent Effects of Nadolol on BAL Eosinophils and Mucin Content

Figure 4A:
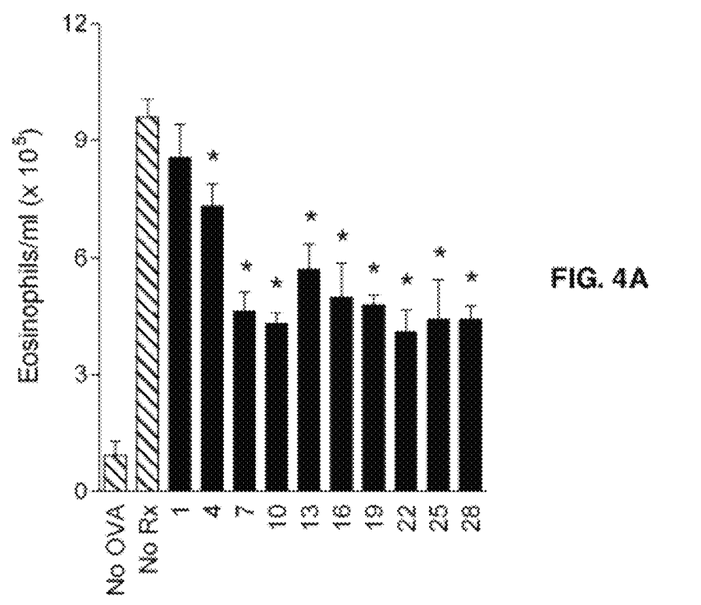
FIGS. 4A-4B illustrate the time-dependant effects of nadolol on airway eosinophils and mucin content. Eosinophil numbers in BAL (FIG. 4A) and mucin content (FIG. 4B) in the airway epithelia of mice were analyzed from control mice (No OVA), OVA immunized mice administered vehicle (No Rx), or nadolol. BAL and morphometric quantification of the mucin volume density was assessed from the various groups, at different duration of nadolol administration. Values are the means±SEM of data from 4 to 5 mice in each group (n=4-5); and *, indicate significant difference compared to No Rx, $P<0.05$.
Figure 4B:
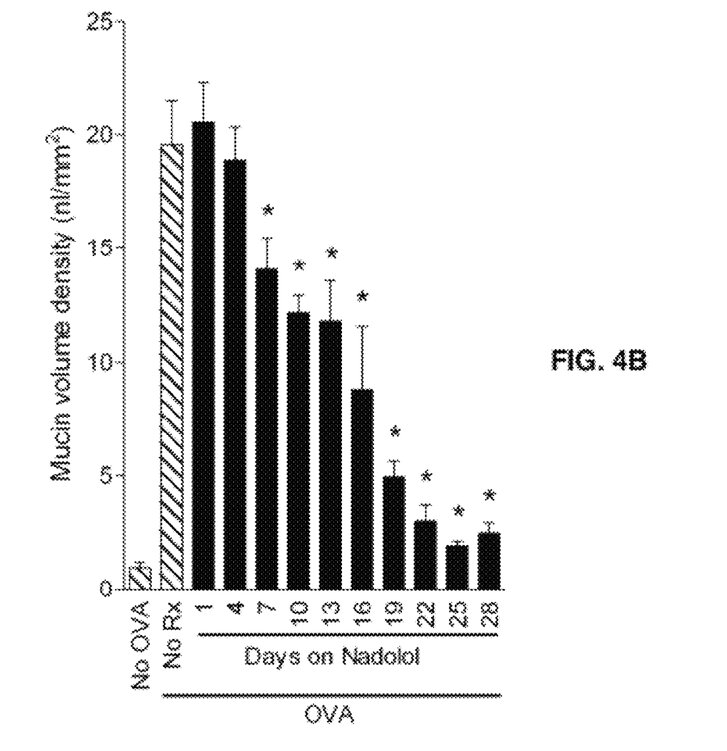

To determine the time-course of the effect of beta-adrenergic inverse agonists, another set of experiments is performed in which exposure to nadolol is begun at different time points after the completion of the sensitization process. Maximal reductions in airway eosinophilia from OVA S/C are detected at day 7 (~50%), and remain maximal throughout the course of nadolol administration (FIG. 4A). Similarly, significant reductions in mucin volume density are also observed after 7 days of treatment with nadolol in OVA S/C mice in comparison to vehicle treated control mice, but surprisingly do not achieve maximal effect until day 22 (FIG. 4B).

EXAMPLE 11

Administration of Dexamethasone and Nadolol Individually, or in Combination, Alters Th2 Cytokines in BAL Fluid Cytokine levels were measured after a single concentration of nadolol (250 ppm), or dexamethasone (4.0 mg/kg/day), or the combination of nadolol 25 ppm and dexamethasone 0.4 mg/kg/day; and at a single time point 24 h after challenge. The levels of Th2 (IL-5, IL-13, eotaxin, MDC, TARC) but not of Th1 (IL-12, IFNγ) cytokines were increased in BAL fluid of mice sensitized and challenged (S/C) with OVA. Among the Th17 cytokines and inflammatory cytokines, IL-17, IL-23, IL-1α, and IL-6 did not change while TNFα and TGFβ1 rose modestly. Table 1 provides cytokine levels and percentages in the drug treatment groups.

Treatment with either high-dose dexamethasone or high-dose nadolol decreased Th2 cytokine levels, TGFb1, and TNFa nearly to their baseline in the presence of OVA S/C, but caused either no change or a rise in Th1 and Th17 cytokines and in IL-α1 and IL-6. As reported above for eosinophils in BAL and mucin content, the effects of co-administration of intermediate-dose dexamethasone and nadolol were comparable to administration of either drug in high doses alone.

TABLE 1

| pg/ml | | No OVA | OVA | | |
|---|---|---|---|---|---|
| | | | No Rx | Dex | Nad | Dex + Nad |
| $T_h2$ | IL-5 | 97 ± 40.1* | 211 ± 39.0 (218%) | 63 ± 19.3 (30%)* | 118 ± 33.0 (56%)* |
| | IL-13 | 8 ± 3.0* | 45 ± 7.0 (563%) | 12 ± 5.0 (27%)* | 6 ± 2.0 (13%)* |
| | eotaxin | 21 ± 8.1* | 45 ± 9.0 (214%) | 12 ± 2.0 (27%)* | 36 ± 6.0 (80%) |
| | MDC | 44 ± 21.0* | 184 ± 48.0 (418%) | 10 ± 1.0 (5%)* | 49 ± 11.1 (27%)* |
| | TARC | 537 ± 369.0* | 3088 ± 1259 (575%) | 475 ± 47.0 (15%)* | 593 ± 223.5 (19%)* |
| $T_h1$ | IL-12p70 | 7 ± 1.1 | 5 ± 2.0 (71%) | 9 ± 1.3 (180%) | 7 ± 1.0 (140%) |
| | IFNg | 4 ± 1.3 | 6 ± 1.0 (150%) | 90 ± 1.1 (1500%) | 7 ± 1.1 (116%) |
| $T_h17$ | IL-17 | 1 ± 0.2 | 2 ± 0.3 (200%) | 2 ± 0.4 (0) | 1 ± 0.2 (50%) |
| | IL-23 | 46 ± 20.4 | 37 ± 12.1 (80%) | 74 ± 10.0 (200%) | 28 ± 4.3 (76%) |
| OTHER | IL-1a | 14 ± 2.2 | 15 ± 5.4 (107%) | 35 ± 7.1 (233%)* | 11 ± 5.0 (73%) |
| | IL-6 | 12 ± 2.0 | 24 ± 7.0 (200%) | 39 ± 28.2 (163%) | 21 ± 10.0 (88%) |
| | TNFa | 26 ± 8.3* | 62 ± 12.0 (238%) | 14 ± 1.0 (23%)* | 33 ± 8.0 (53%)* |
| | TGFβ1 | 4378 ± 1816* | 13210 ± 1512 (302%) | 4675 ± 792 (35%)* | 5891 ± 710 (45%)* |

Definition of abbreviations in Table 1 are $T_h$1/2/17=T helper (1, 2, or 17) type inflammation; MDC=macrophage-derived chemokine; TARC=thymus and activation regulated chemokine; IL=interleukin-1a, IL-5, IL-6, IL-12p70, IL-13, IL-17, IL-23; IFNγ=interferon gamma; TNFα=tumor necrosis factor alpha; TGFβ1=transforming growth factor betal. The percentage from No Rx is in comparison to No OVA for each cytokine, while percentage of each drug treatment group [Dex (4.0 mg/kg/day); Nad (250 ppm); and Dex+Nad (0.4 mg/kg/day+25 ppm)] is in comparison to No Rx. Values are the means±SEM of data from 4 mice in each group (n=4); and *, indicate significant difference compared to No Rx, P<0.05.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

The following references may have been cited herein:
1. Jack, D. 1997. *J Pharm Pharmacol* 49 Suppl 3:17-18.
2. Barnes, et al., 1988. *Pharmacol Rev* 40:49-84.
3. Fahy, J. V. 2002. *Chest* 122:320S-326S.
4. Rogers, D. F. 2004. *Curr Opin Pharmacol* 4:241-250.
5. Odhiambo, et al., 2009. *The Journal of Allergy and Clinical Immunology* 124:1251-1258 e1223.
6. Harris, et al., 1973. *Clin Allergy* 3:243-248.
7. Barnes, et al., 1998. *Pharmacol Rev* 50:515-596.
8. Brown, et al., 1996. *The Journal of Experimental Medicine* 184:1295-1304.
9. Roth, et al., 1996. *The Journal of Experimental Medicine* 184:539-548.
10. Corry, et al., 1996. *The Journal of Infectious Diseases* 174:440-443.
11. Jack, D. 1971. *Postgrad Med J* 47:Suppl:8-11.
12. Jack, D. 1971. *Br Med J* 2:708-709.
13. van Gestel, et al., 2008. *Am J Cardiol* 102:192-196.
14. Dickey, et al., 2010. *Current Opinion in Pharmacology* 10:254-259.
15. Weatherall, et al., 2009. *Respirology* 14:983-990.
16. Hanania, et al., 1995. *The Journal of Allergy and Clinical Immunology* 96:571-579.
17. Hanania, et al., 1995. *The American Journal of Medicine* 98:196-208.
18. Rossi, et al., 2007. *Pulmonary Pharmacology & Therapeutics* 20:23-35.
19. Nguyen, et al. 2008. *Am J Respir Cell Mol Biol* 38:256-262.
20. Callaerts-Vegh, et al., 2004. *Proc Natl Acad Sci USA* 101:4948-4953.
21. Hanania, et al. 2008. *Pulmonary Pharmacology & Therapeutics* 21:134-141.
22. Hanania, et al., 2010. *The European Respiratory Journal: Official Journal of the European Society for Clinical Respiratory Physiology* 36:963-965.
23. Lin, et al., 2008. *Pulm Pharmacol Ther* 21:115-124.
24. Nguyen, et al., 2009. *Proc Natl Acad Sci USA* 106:2435-2440.
25. Trifilieff, et al., 2000. *American journal of physiology. Lung cellular and molecular physiology* 279:L1120-1128.
26. Karpel, et al., 2010. *Annals of Allergy, Asthma & Immunology* 105:465-470.
27. Bond, et al. 1995. *Nature* 374:272-276.
28. Wisler, et al., 2007. *Proc Natl Acad Sci USA* 104:16657-16662.
29. Evans, et al. 2004. *Am J Respir Cell Mol Biol* 31:382-394.

What is claimed is:

1. A pharmaceutical composition comprising a combination of (a) about 0.1 mg to about 0.4 mg of dexamethasone and (b) about 5 ppm to about 25 ppm of nadolol, optionally in the form of their racemates, their enantiomers, their diastereomers and mixtures thereof, and optionally their pharmacologically-compatible acid addition salts, wherein the active ingredients (a) and (b) form part of a single composition.

2. The composition according to claim 1 wherein ingredients (a) and (b) are provided together with instructions for simultaneous, concurrent, separate or sequential administration, in a kit of parts for the treatment of a patient suffering from or susceptible to asthma or chronic obstructive pulmonary disease.

3. The composition according to claim 1 wherein the active ingredients (a) and (b) are in the form a dry powder suitable for inhalation.

4. The composition according to claim 1, further comprising a pharmaceutically acceptable excipient selected from mono-, di- or polysaccharides and sugar alcohols.

5. A method of treating a human or animal patient suffering from or susceptible to chronic obstructive pulmonary disease, said method comprises simultaneously, concurrently, separately or sequentially administering to said patient an effective amount of the pharmaceutical composition of claim 1.

6. The method according to claim 5, wherein nadolol in said pharmaceutical composition is administered in an amount of from about 1% to about 100% of the FDA approved dose.

7. The method according to claim 5, wherein dexamethasone in said pharmaceutical composition is administered in an amount of from about 0.1% to about 100% of the FDA approved doses of the corticosteroid.

8. A method of treating asthma characterized by an increase in allergen-induced airway hyper-responsiveness and mucus-containing cells in a mammalian subject, said method comprising administering to said subject an effective amount of the pharmaceutical composition of claim 1 in an amount sufficient to decrease lung inflammation in the subject, thereby treating the asthma in said subject.

9. The method according to claim 8, wherein nadolol in said pharmaceutical composition is administered in an amount of from about 1% to about 100% of the FDA approved dose.

10. The method according to claim 8, wherein dexamethasone in said pharmaceutical composition is administered in an amount of from about 0.11% to about 100% of the FDA approved dose.

11. The method according to claim 8, wherein the allergen-induced airway hyper responsiveness and the allergen-induced increase in mucus-containing cells are decreased after administration of said pharmaceutical composition.

12. The method according to claim 8, wherein airway eosinophilia is reduced after administration of said pharmaceutical composition.

13. The method according to claim 8, wherein levels of TGFβ1 and TNFα are reduced after administration of said pharmaceutical composition.

* * * * *